United States Patent [19]

Ozdemir

[11] Patent Number: 4,870,275
[45] Date of Patent: Sep. 26, 1989

[54] CIRCULATING RAMAN-MEDIA LASER RADAR METHOD AND APPARATUS FOR REMOTE MEASUREMENT OF GASES IN THE ATMOSPHERE

[75] Inventor: Phillip Ozdemir, Plainfield, N.J.

[73] Assignee: Skyborne Exploration Canada, Limited, New York, N.Y.

[21] Appl. No.: 191,052

[22] Filed: May 6, 1988

[51] Int. Cl.$^4$ ............................................. G01N 15/07
[52] U.S. Cl. ................................... 250/574; 250/575; 356/301
[58] Field of Search ................ 250/574, 575; 356/301, 356/343, 342, 335, 336, 337, 338, 339, 340, 341, 435, 436, 437, 438–444

[56] References Cited

U.S. PATENT DOCUMENTS

| | | | |
|---|---|---|---|
| 4,071,298 | 1/1978 | Falconer | 356/301 |
| 4,450,356 | 5/1984 | Murray et al. | 250/339 |
| 4,648,714 | 3/1987 | Benner et al. | 356/301 |

FOREIGN PATENT DOCUMENTS 808760  5/1969  Canada ............................. 250/254

OTHER PUBLICATIONS

Alden et al, Remote Measurement of Atmospheric Mercury Using Differential Absorption Lidar, vol. 7, No. 5, Optics Letters, p. 221, May 1982.
A Continuously Tunable Sequential Stokes Raman Laser, P. Rabinowitz et al, Exxon Research and Engineering Company, Abstract.

Primary Examiner—David C. Nelms
Assistant Examiner—William L. Oen
Attorney, Agent, or Firm—Cushman, Darby & Cushman

[57] ABSTRACT

Gases in the atmosphere are detected remotely using a Raman-shifted excimer/dye laser beam formed by passing an excimer/dye laser beam through a circulating-medium Raman-shifting cell which significantly increases the measurement repetition rate and allows for the production of an infinite number of different wavelengths for measurement. The Raman-active medium is continuously circulated so that the inputted laser beam passes through the Raman-active medium when the molecules of the medium in the optical path are at their ground energy level state. The Raman cell is then tuned to provide a first wavelength, preselected for nonabsorption by the gases to be detected, which is transmitted through the gases to be detected toward an object capable of reflecting the beam back. The Raman cell is also tuned to provide a second wavelength, preselected for being highly absorbed by the gases to be detected, which is then transmitted and similarly reflected. The presence and quantity of the gases are then determined by the difference in the amount respectively absorbed at the two wavelengths.

7 Claims, 3 Drawing Sheets

CIRCULATING RAMAN-MEDIA LASER RADAR METHOD AND APPARATUS FOR REMOTE MEASUREMENT OF GASES IN THE ATMOSPHERE

BACKGROUND OF THE INVENTION

1. Field of the Invention

This invention relates to the detection of gases using laser beams. More particularly, this invention relates to the remote detection of gases in the atmosphere using the outputs of excimer/dye lasers which have been frequency-shifted in circulating-media Raman cells.

2. Description of the Prior Art

The detection of gases in the atmosphere using laser beams in the infrared region is known to those skilled in the art. Canadian Pat. No. 808,760, for example, describes the detection of hydrocarbon gases using noble gas lasers such as a helium-neon laser mounted on an aircraft. The method comprises the use of two laser beams of slightly different wavelengths, either from the same laser or from different lasers. One preselected wavelength is highly absorbed by the gas to be detected while the other is not highly absorbed, thereby providing a differential coefficient. The laser beams pass through the gas in question and are reflected back to a common detection source which measures the intensities of the two beams. Any difference in the measured intensities determines the presence and quantity of the gas in question. Dust, water droplets and other light scattering materials in the atmosphere act in a similar manner on the two beams and are thus factored out.

While such detection schemes should be highly satisfactory in determining the presence or absence of preselected gases, in practice they are restricted by the limited number of wavelengths emitted by such lasers and the number of interfering gases possibly present in the atmosphere either alone or in combination with the other gases. For example, the most popular and frequently used of such lasers, the helium-neon laser, only emits 10 possible wavelengths in the frequency band where detection takes place. While these particular wavelengths have been found selective with respect to methane, they are not useful for detection of ethane, for example.

Other lasers may be substituted for the helium-neon laser to permit selective detection of other gases such as ethylene, which cannot be detected satisfactorily with the helium-neon laser. As described by E. R. Murray and J. E. van der Laan in an article entitled "Remote Measurement of Ethylene" in *Applied Optics*, Volume 17 at page 814 (Mar. 1, 1978) and in U.S. Pat. No. 4,450,356, for example, the detection of ethylene or other gases in the atmosphere may be accomplished by selective absorption of wavelengths emitted by a $CO_2$ laser. Also, as taught by Alden et al. in "Remote Measurement of Atmospheric Mercury Using Differential Absorption Lidar", Optics Letters, Vol. 7, No. 5, May 1982, sulphur dioxide, nitrogen dioxide and mercury may be remotely measured in the ultraviolet spectral region using an Nd:YAG laser.

However, in such systems for the detection of gases in the atmosphere, there is still a need for more flexible laser systems which can emit a sufficient number of different wavelengths in wavelength regions for remote gas detection so that spectral matching with the desired gases may be accomplished. Some gases may interfere with the desired gases by having differential absorption coeffcients at a particular pair of wavelengths that are sufficiently large so that the gases cannot be distinguished from each other. Accordingly, more wavelengths in the desired micron wavelength region are necessary so that more particularized wavelength pairs for analysis of desired gases may be selected. One such technique is disclosed by the above-mentioned Murray et al U.S. Pat. No. 4,450,356, wherein a first $CO_2$ laser beam is passed through a frequency doubling crystal and summed with a second $CO_2$ laser beam. Each $CO_2$ laser in the Murray et al system is capable of being tuned to 80 different frequencies to provide a total of 6400 frequencies for selection. Although this represents a significant improvement in frequency selection, it is desirable to provide an unlimited number of such combinations to improve measurement accuracy.

It is known that the number of wavelengths emitted by a laser source can be increased and the frequency range changed by the use of Raman shifting. For example, Alden et al disclose that Raman shifting may be used in conjunction with an Nd:YAG laser to reach the mercury absorption line. In addition, Paul Rabinowitz, Bruce Perry and N. Levinos in an article entitled "A Continuously tunable Sequential Stokes Raman Laser" describe frequency shifting of excimer/dye laser radiation using a high pressure hydrogen cell with a confocal resonator to produce multiple gain paths in a Ramanactive medium. All things being equal, the system described by Rabinowitz et al. should allow for an unlimited number of operating wavelengths, and the problem of limited target gas selection in the above-described systems would appear to be solved.

However, in the application of such technology for the detection of gases in the atmosphere, there is still a need for a system capable of making more sensitive differential measurements, for the present state of the art considers only stationary Raman-active media. In such systems with stationary Raman-active media, the excited medium may not relax before the next firing of the laser. Thus, not only is the repetition rate greatly diminished, resulting in repetition rates too low for remote measurement by aircraft, for example, but the beam may be not be effectively shifted when the Raman-active medium has not had time to relax to its ground energy level. Accordingly, lidar systems constructed using such techniques for wavelength optimization have been found to yield sensitivities lower than that useful for many applications such as remote gas measurement.

When making measurements from a rapidly moving airborne platform for gases present in the near surface atmosphere, such as those from chemical plant spills, the problems of low repetition rate lidar systems using Raman-shifting in stationary media become even more apparent. Thus, it is still necessary to increase the sensitivity and repetition rate of systems for remotely measuring gases in the atmosphere such the above-mentioned lidar systems of the prior art in order to achieve more reliable measurements.

SUMMARY OF THE INVENTION

The purpose of the present invention is to overcome the disadvantages in the prior art systems noted above by increasing the sensitivity and repetition rate at which gases in the atmosphere may be measured remotely, as from an aircraft.

This is accomplished in accordance with the present invention using a circulating Raman-active medium. More particularly, it has now been discovered that differential absorption lidar can be used to detect a number of gases in the atmosphere by passing excimer/dye laser radiation through a circulating Raman-active medium so as to significantly increase the measurement repetition rate. The resultant system is capable of effectively producing an infinite number of different wavelengths in the 3 micron region where numerous gases, including light hydrocarbons, selectively absorb radiation, and this system may operate at repetition rates in excess of 250 times per second.

BRIEF DESCRIPTION OF THE DRAWINGS

These and other objects and advantages of the present invention will become more apparent and more readily appreciated from the following description of the presently preferred exemplary embodiment thereof, taken in conjunction with the accompanying drawings, of which.

DETAILED DESCRIPTION OF THE PRESENTLY PREFERRED EXAMPLARY EMBODIMENT

Figure 1:
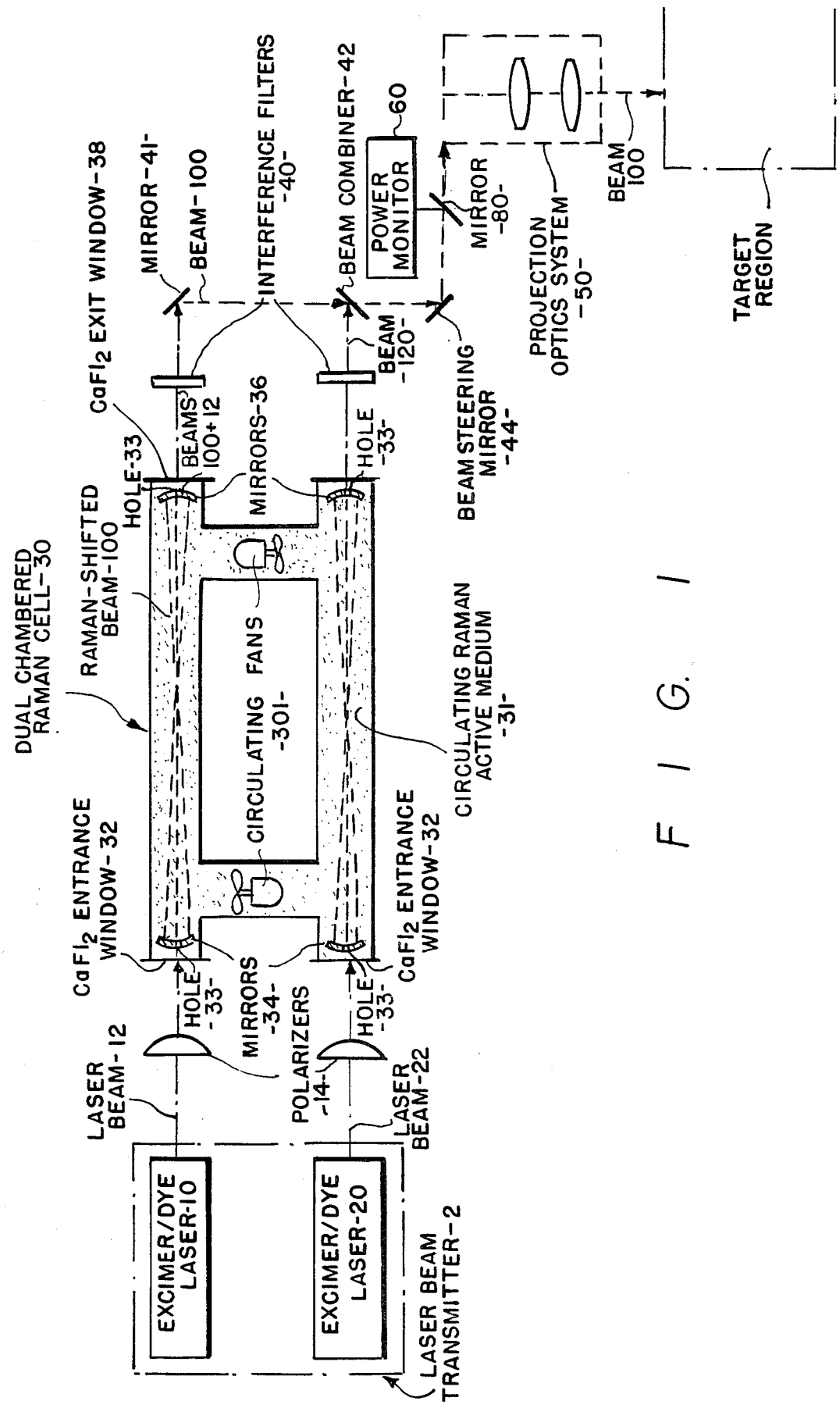
FIG. 1 is a schematic depiction of the laser beam transmitter of the preferred embodiment.

Referring to FIG. 1, a laser beam transmitter 2 is schematically shown comprising a first excimer/dye laser source 10 and a second excimer/dye laser source 20. Laser sources 10 and 20 comprise a high repetition rate excimer-pumped dye laser system such as that available from Lambda Physik in Acton, Massachusetts. One or both sources should be tunable to a particular wavelength using suitable tuning means such as a diffraction grating.

Figure 3:
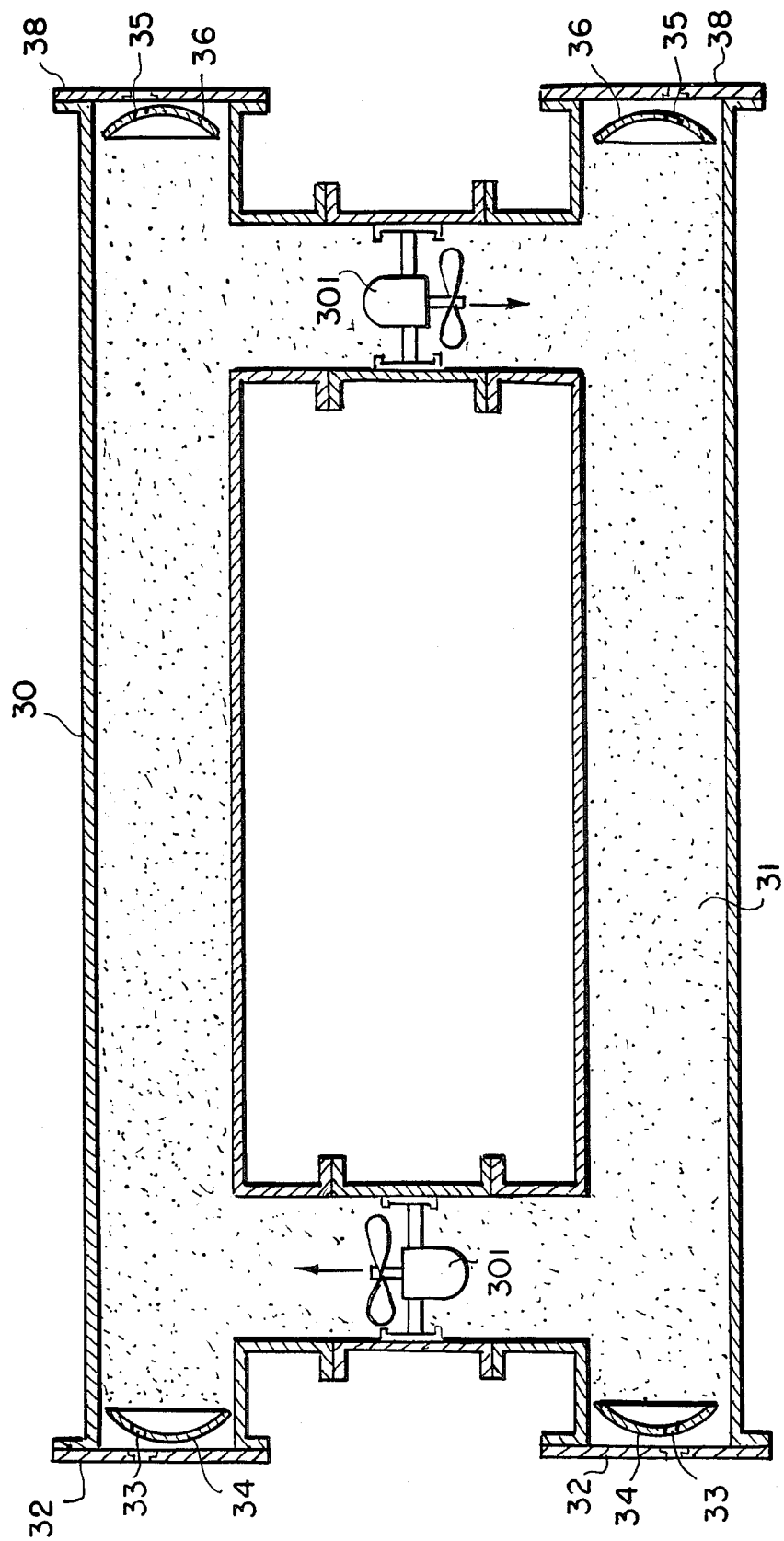
FIG. 3 is a more detailed schematic view of the dual chambered Raman Cell used in the laser beam transmitter of FIG. 1.

A laser beam 12 from source 10 is passed through a circular polarizer 14 to increase the Raman-interaction cross-section of the beam 12 for interaction with the circulating Raman-active medium 31 in dual-chambered Raman cell 30 (shown in more detail in FIG. 3). Laser beam 12 is passed through calcium fluoride entrance window 32 and then through a hole 33 in mirror 34. The beam 12 then passes through circulating Raman-active medium 31 to produce a beam of Raman-shifted radiation 100, with the shifted wavelength being characteristic of the particular Raman-active medium being employed (in the case of hydrogen gas as the Raman-active medium, for instance, the wavelength shift is N(4155 cm)−1, where N=±1, 2, 3, . . . ). Beam 12 then bounces off mirror 36 and is returned to mirror 34. This process continues several times until beam 12 and Raman-shifted beam 100 both exit through hole 35 in mirror 36, and then exit through calcium fluoride exit window 38. Energy from beam 12 is thus transferred to Raman-shifted beam 100 on each pass through the medium, and this multi-pass technique allows practical packaging of the long interaction length which is necessary to generate appreciable energy at the Raman-shifted wavelength.

The Raman cell 30 effects absolute frequency changes in the inputted laser beam by shifting the laser light's frequency in the spectral bandwidth of the laser light. More particularly, different gases may be used in the Raman cell to change the frequencies of the pump laser output by adding a certain number of angstroms to the inputted laser light's wavelength. This occurs since a pulse of the inputted light interacts with a dipole moment of the Raman-active medium to produce a non-linear effect. In other words, different molecules of the light experience differing strobe shifts so that it is possible to continuously vary the frequency output of the Raman cell 30 by keeping the Raman active medium 31 circulating in the Raman cell 30. Also, it is desirable to use a common gas in the Raman cell 30 as Raman-active medium 31 to increase the stability of such shifting. By thus passing the laser beams through such a common circulating Raman-medium 31, which is kept circulating by fans 301, the tuning range of the inputted optically pumped laser beams may be extended to ranges acceptable for laser prospecting with sufficient energy without the need for complicated apparatus.

Referring back to FIG. 1, the Raman-shifted laser beam 100 and laser beam 12 outputted by Raman cell 30 are next passed through interference filter 40, which allows Raman-shifted beam 100 to pass, but does not allow beam 12 to pass. The filtered Raman-shifted radiation 100 then is reflected by mirror 41 and passed through beam combiner 42 to beam steering mirror 44 before being transmitted to the measurement region of interest by projection optics system 50 as shown. Beam steering mirror 44 directs the laser beam from each laser down to the target region along the optical axis of the optics system 50, thereby ensuring that the laser beam irradiated area is always kept within the optical field of view of optics system 50.

Since a differential absorption measurement requires two wavelengths for measurement, it is then necessary to generate a second Raman-shifted laser beam 120 having a slightly different wavelength than the first beam 100. This beam must be generated within about 100 microseconds of the first beam 100 in order to minimize the scintillation effects of the atmosphere. This beam 120 is generated in the second chamber of the dual-chambered Raman-shifter 30 from laser beam 22 in the same manner described above for the generation of the first output beam 100. This double-barrelled nature of the Raman-shifting apparatus 30 in the preferred embodiment is easier to fabricate and requires less space and is thus preferred, although not necesary.

Figure 2:
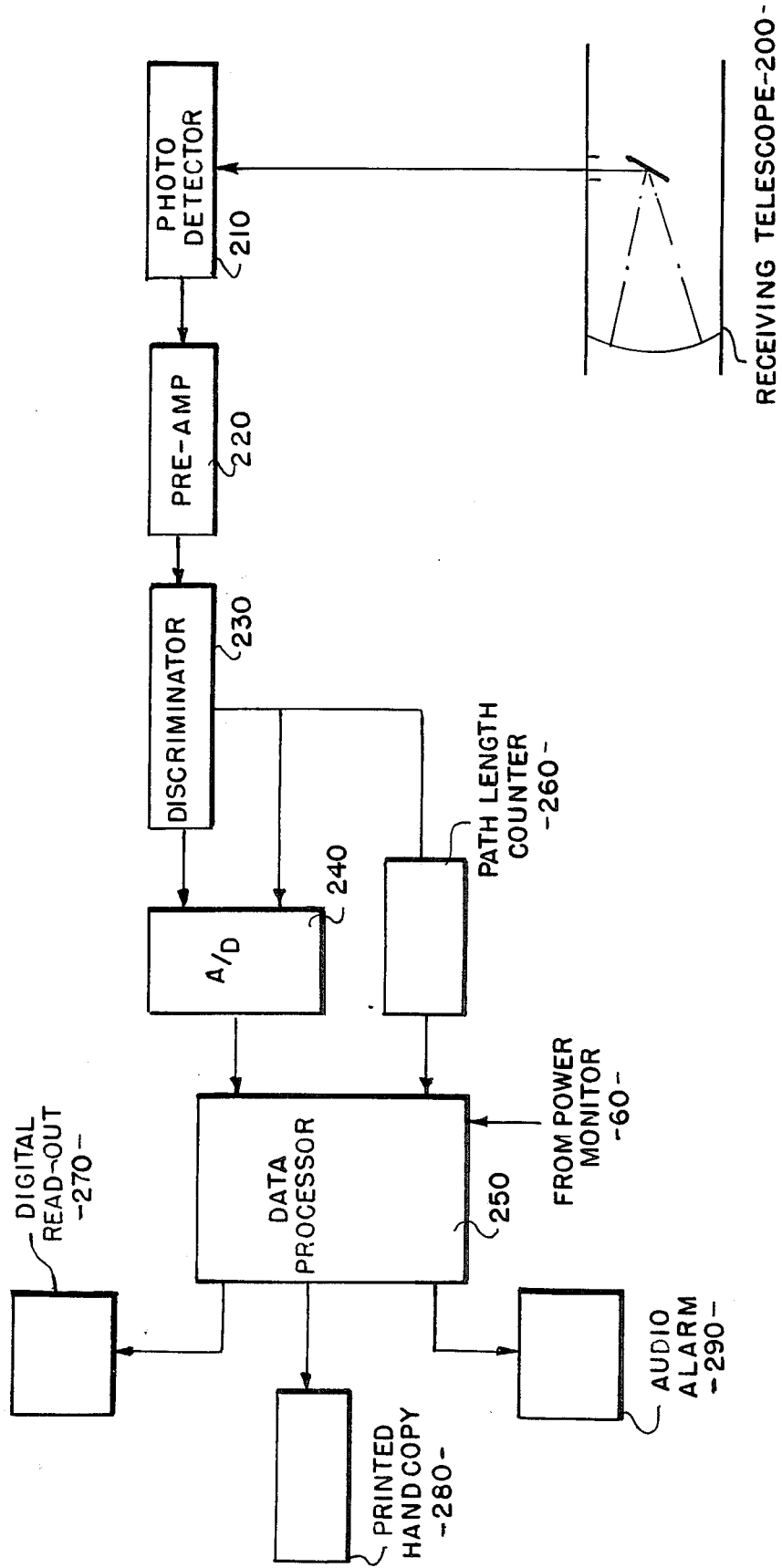
FIG. 2 is a schematic depiction of the receiving system of the preferred embodiment.

Referring now to FIG. 2, after travelling to the target region, reflecting off topographic or man-made targets, and returning to the measurement platform, both beams are sequentially collected by receiving telescope 200. Receiving telescope 200 may be a wide aperture Newtonian telescope such as the type manufactured by Coulter Optics in Idyllwild, Calif. The beams are then sequentially detected by a photovoltaic or photoconducting detector 210 at the receiver. In the preferred embodiment, a liquid nitrogen-cooled InSb detector, available from Santa Barbara Research, Goleta, Calif., may be used for this purpose.

The signals resulting from detector 210 are amplified by preamplifier 220. Discriminator 230 then detects the presence of these signals and supplies a gate signal to a gated analog-to-digital converter 240. The signals representing the received intensities of both beams are then sequentially digitized by analog-to-digital converter 240.

In addition to the received signal preprocessing, data required by the data processing system (microcomputer) 250 includes information from power monitor system 60 and path length counter 260. Power monitor 60, with electronics similar to the receiver, detects the small fraction of transmitted power passing through mirror 80, and the detected power is used for normalizing the transmitted energy. Path length counter 260, on the other hand, provides range information.

The signals from analog-to-digital converter 240, power monitor 60 and path length counter 260 are then processed by the data processing system (micro-computer) 250 to determine the amount of absorption by the gas in question. This measurement is carried out on both beams, the first beam having a wavelength which is highly absorbed by the gas to be detected, while the second beam has a wavelength which is weakly absorbed. The backscattered signal from the first frequency pulse is used to calibrate the gain of the system and the reflectance of the topographic target. The ratio of the backscattered signals between the two frequencies thus is a direct measure of the product of concentration and path length, and because the technique involves the measurement of a differential rather than an absolute magnitude, it is self-calibrating.

The data processing system 250 calculates the path-averaged concentration of the detected gas by first forming a ratio of the return signal at the two wavelengths, then taking the logarithm of the ratio, and finally multiplying this quantity by the inverse of the differential absorption coefficient times the range to the target. The target range varies considerably even for a given application and is automatically established by the time of flight of the laser pulses. The data processing system 250 may them output a continuous digital readout on monitor 270, a printed hardcopy on printer 280, or an audio alarm on alarm 290 for concentrations above a certain threshold.

As noted above, the Raman-active medium 31 of Raman cell 30 may be kept in continuous circulation by circulator fans 301; therefore, it is possible to fire lasers 10 and 20 a very short time after the first measurement cycle has been completed. When using previous Raman-shifter designs employing stationary Raman-active media, however, it is not possible to fire lasers 10 and 20 so close together in time since it is necessary to wait for the Raman-active medium to return to its relaxed state or to replace the old gas with new gas between laser firings, which requires at least 1 ms. Thus, molecules in the optical paths of unshifted pump beams 12 and 22 in the prior art may not have had time to relax to their ground energy level state before the next pulse is encountered. They are therefore not available to act as Raman "scatterers" and cannot effectively shift the wavelength of the incoming pump beam.

Since the accuracy of a lidar system increases as the square root of the number of measurement pulse pairs which are used, the measurement systems which can perform a greater number of measurements per unit time are more accurate. Excimer/dye laser systems have been constructed which have pulse repetition rates of up to 250 Hz. Using Raman-shifting devices with stationary media as in the prior art, however, it would be necessary to limit the pulse repetition rates of such lasers to the order of 1-10 Hz in a lidar system. By contrast, in accordance with the present invention, pulse repetition rates of 250 Hz can easily be achieved by using a Raman-shifting device in which the Raman-active medium is kept circulating. Thus, increases in the accuracy of measurement of 5 to 15 $((250/10)^{\frac{1}{2}}$ to $(250/1)^{\frac{1}{2}})$ times are achievable in accordance with the present invention.

Although only a single exemplary embodiment of this invention has been described above in detail, those skilled in the art will readily appreciate the many modifications are possible in the exemplary embodiment without materially departing from the novel teachings and advantages of the invention. For example, a single laser source capable of firing laser pulses in rapid succession may be used in place of the two excimer/dye laser sources disclosed. Accordingly, this and other such modifications are intended to be included within the scope of the invention as defined in the following claims.

What is claimed is:

1. A system for detecting the presence of one or more gases in the atmosphere, comprising:
   means for respectively generating coherent first and second light beams at first and second wavelengths in the visible portion of the spectrum;
   means for Raman-shifting said first light beam so as to change the frequency of said first light beam, said Raman-shifting means including a Raman-active medium and means for continuously circulating said medium so that said first light beam passes through said medium in the medium's relaxed energy state so as to provide a first Raman-shifted light beam having a wavelength which is different from said second wavelength, one of either said first Raman-shifted light beam or said second light beam having a wavelength which is readily absorbed by said one or more gases to be detected, while the other light beam has a wavelength which is not readily absorbed by said one or more gases;
   means for transmitting at least said first Raman-shifted light beam outputted by said Raman-shifting means through the atmosphere towards an object capable of reflecting light, said object being in an area to be investigated for said one or more gases; and
   means responsive to light reflected by said object for measuring the intensity of light reflected by said object and determining the presence or absence of said one or more gases in said area by measuring the difference in the intensity of light received at the wavelength of said first Raman-shifted light beam and said second wavelength, respectively.

2. The system according to claim 1, wherein said light transmitting means comprises mirrors positioned so as to transmit at least said first Raman-shifted light beam coaxial to said detecting means so that the light beams reflected back from said object may be readily measured.

3. The system according to claim 1, wherein said light generating means comprises first and second excimer/dye laser sources.

4. The system according to claim 1, wherein said means for continuously circulating said medium comprises at least one circulator fan for keeping said Raman-active medium continuously circulating.

5. A system for the detection of one or more preselected gases in the atmosphere, comprising:
   first and second excimer/dye lasers for respectively generating first and second laser beams at first and second wavelengths in the visible portion of the spectrum;
   a dual chambered Raman shifter for Raman-shifting said first and second laser beams so as to change the frequency of said first and second laser beams, said Raman shifter including a Raman-active medium and means for continuously circulating said medium so that said first and second laser beams pass through said medium in the medium's relaxed energy state so as to provide first and second Raman-shifted laser beams respectively having a first Raman-shifted wavelength which is readily absorbed by said one or more preselected gases and a second Raman-shifted wavelength, different from said first Raman-shifted wavelength, which is not readily absorbed by said one or more preselected gases;

means for transmitting at least one of said first and second Raman-shifted laser beams toward a target through the atmosphere, said target being in an area which may contain said one or more preselected gases, said gases selectably absorbing the Raman-shifted light outputted by said first and second excimer/dye lasers at preselected frequencies; and means for detecting the intensity of a signal reflected back from said target and determining the presence or absence of said one or more preselected gases by measuring the differences in intensity of the reflected signal at said first and second Raman-shifted wavelengths, respectively.

6. The system according to claim 5, wherein said means for continuously circulating said medium comprises at least one circulator fan for keeping said Raman-active medium continuously circulating.

7. A method for detecting the presence of one or more preselected gases in the atmosphere, comprising the steps of:

generating first and second laser beams from a laser beam source, each laser beam having a frequency in the visible portion of the spectrum;

passing at least one of said first and second laser beams through a Raman-active medium;

continuously circulating said Raman-active medium so that said at least one laser beam passes through said medium in the medium's relaxed energy state so as to change the wavelength of said at least one laser beam;

tuning said first laser beam so that it has a first frequency which is highly absorbed by said one or more preselected gases and said second laser beam so that it has a second frequency, different from said first frequency, which is not highly absorbed by said one or more preselected gases;

transmitting at least one of said tuned first and second laser beams through the atmosphere toward a reflecting target in an area to be investigated for said one or more preselected gases;

detecting the reflected beams reflected by said reflecting target; and comparing the intensity of the reflected output beam at said first and second frequencies to determine the amount of absorption by said one or more preselected gases at said first and second frequencies to thereby determine the presence or absence of said one or more preselected gases in said area.

* * * * *